United States Patent [19]

Shirk

[11] Patent Number: 6,096,997
[45] Date of Patent: Aug. 1, 2000

[54] METHOD OF ASSEMBLING AN IGNITER INCLUDING INFRARED TESTING OF HEATING ELEMENT AND WELDS

[75] Inventor: Bryan W. Shirk, Mesa, Ariz.

[73] Assignee: TRW Inc., Lyndhurst, Ohio

[21] Appl. No.: 09/458,482

[22] Filed: Dec. 9, 1999

Related U.S. Application Data

[63] Continuation-in-part of application No. 08/921,723, Aug. 29, 1997.

[51] Int. Cl.$^7$ ............................. F24B 3/12; F24B 3/19; G01N 25/72; G01R 31/00
[52] U.S. Cl. ..................... 219/260; 219/270; 228/104; 374/5; 324/501; 324/502; 29/593; 102/202.7; 102/202.9; 102/530
[58] Field of Search ............................... 219/260, 270, 219/522, 109; 228/103–105; 374/5; 324/501, 750, 753, 158.1, 502; 102/202.9, 202.7, 530, 531; 280/736, 741; 29/593

[56] References Cited

U.S. PATENT DOCUMENTS

| | | |
|---|---|---|
| 3,463,007 | 8/1969 | Jones et al. . |
| 3,686,934 | 8/1972 | Farrand et al. . |
| 3,803,413 | 4/1974 | Vanzetti et al. . |
| 4,214,164 | 7/1980 | Traub et al. . |
| 4,481,418 | 11/1984 | Vanzetti et al. . |
| 4,540,293 | 9/1985 | Shores . |
| 4,696,101 | 9/1987 | Vanzetti et al. . |
| 4,854,724 | 8/1989 | Adams et al. . |
| 5,283,416 | 2/1994 | Shirk . |
| 5,348,344 | 9/1994 | Blumenthal et al. . |
| 5,360,960 | 11/1994 | Shirk . |
| 5,403,036 | 4/1995 | Zakula et al. . |
| 5,572,181 | 11/1996 | Kiryu et al. . |
| 5,733,041 | 3/1998 | Sedlak et al. . |
| 5,939,660 | 8/1999 | Fogle, Jr. ............................. 102/202.7 |
| 5,942,717 | 8/1999 | Pathe et al. ......................... 102/202.2 |

FOREIGN PATENT DOCUMENTS 55-10527   1/1980   Japan .

*Primary Examiner*—John A. Jeffery
*Attorney, Agent, or Firm*—Tarolli, Sundheim, Covell, Tummino & Szabo L.L.P.

[57] ABSTRACT

A method of assembling an igniter (24) for a gas generating composition (18) comprises providing a pair of spaced apart electrodes (40 and 42) and providing a heat ignitable material (46). A heating element (44) is spot electrical resistance welded to the electrodes (40 and 42). The heating element (44) has flattened portions (110 and 112) at the spot welds (102 and 104) and a central portion between the spot welds (102 and 104) adapted for contact with the heat ignitable material (46). A test level of electric current is directed between the electrodes (40 and 42) and through the heating element (44) and the spot welds (102 and 104) at a level effective to heat the heating element (44) and the spot welds (102 and 104). The level infrared radiation emitted by the heating element (44) and the spot welds (102 and 104) is sensed, throughout a scanned field which fully encompasses the heating element and the welds, under the influence of the test level of electric current. The sensed levels of infrared radiation emitted by the heating element (44) and the spot welds (102 and 104) are compared. The heat ignitable material (46) is installed in heat transferring relationship with the heating element (44) if the sensed level of infrared radiation emitted by one or both of the spot welds (102 and 104) is greater than the sensed level of infrared radiation emitted by the heating element (44).

5 Claims, 3 Drawing Sheets

METHOD OF ASSEMBLING AN IGNITER INCLUDING INFRARED TESTING OF HEATING ELEMENT AND WELDS

This application is a continuation-in-part of pending application Ser. No. 08/921,723 filed Aug. 29, 1997, assigned to the assignee of the present invention.

FIELD OF THE INVENTION

The present invention relates to an igniter for use in inflating a vehicle occupant protection device, such as an air bag, and particularly relates to a method of assembling the igniter.

BACKGROUND OF THE INVENTION

An inflator for an inflatable vehicle occupant protection device, such as an air bag, may contain pressurized inflation fluid and ignitable material which, when ignited, heats the inflation fluid. Such an inflator may include an igniter containing a small charge of pyrotechnic material. The igniter further contains a bridgewire which is supported in an ignitable heat transferring relationship with the pyrotechnic material. When the air bag is to be inflated, an actuating level of electric current is directed through the bridgewire in the igniter. This causes the bridgewire to become resistively heated sufficiently to ignite the pyrotechnic material. The pyrotechnic material then produces combustion products which, in turn, ignite the ignitable material in the inflator.

The fluid pressure inside the inflator is increased by the heat generated upon combustion of the ignitable material. The inflation fluid then flows outward from the inflator and into the air bag to inflate the air bag more quickly than if the inflation fluid had not been heated and further pressurized.

SUMMARY OF THE INVENTION

The present invention is a method of assembling an igniter for a gas generating composition. The method comprises providing a pair of spaced apart electrodes and providing a heat ignitable material. A heating element is spot electrical resistance welded to the electrodes. The heating element has flattened portions at the spot welds and a central portion between the spot welds adapted for contact with the heat ignitable material. A test level of electric current is directed between the electrodes and through the heating element and the spot welds at a level effective to heat the heating element and the spot welds. The level infrared radiation emitted by the heating element and the spot welds is sensed, throughout a scanned field which fully encompasses the heating element and the welds, under the influence of the test level of electric current. The sensed levels of infrared radiation emitted by the spot welds and the heating element are compared. The heat ignitable material is installed in heat transferring relationship with the heating element if the sensed level of infrared radiation emitted by one or both of the is not greater than the sensed level of infrared radiation emitted by the heating element.

BRIEF DESCRIPTION OF THE DRAWINGS

Further features of the present invention will become apparent to those skilled in the art to which the present invention relates from reading the following description with reference to the accompanying drawings, in which.

DESCRIPTION OF PREFERRED EMBODIMENTS

Figure 1:
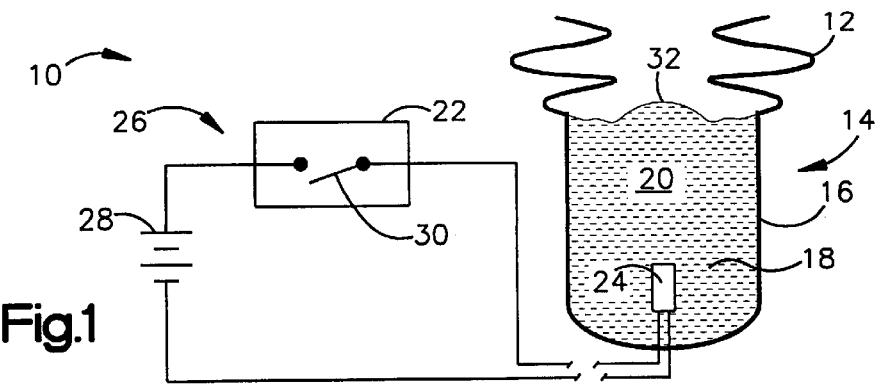
FIG. 1 is a schematic view of a vehicle occupant protection apparatus comprising a preferred embodiment of the present invention.

A vehicle occupant protection apparatus 10 comprising a preferred embodiment of the present invention is shown schematically in FIG. 1. The apparatus 10 includes a particular type of inflatable vehicle occupant protection device 12 which is commonly referred to as an air bag. Other inflatable vehicle occupant protection devices that can be used in accordance with the invention include, for example, inflatable seat belts, inflatable knee bolsters, inflatable head liners or side curtains, and knee bolsters operated by inflatable air bags. The apparatus 10 further includes an inflator 14 which comprises a source of inflation fluid for inflating the air bag 12. When the air bag 12 in inflated, it extends into a vehicle occupant compartment (not shown) to help protect a vehicle occupant from a forceful impact with parts of the vehicle as a result of a crash.

The inflator 14 comprises a container 16 which stores pressurized inflation fluid for inflating the air bag 12. The container 16 also stores ignitable material for heating the inflation fluid. Specifically, the container 16 in the preferred embodiment of the present invention stores a pressurized, combustible mixture of gases 18 in a storage chamber 20. The combustible mixture of gases 18 includes a primary gas and fuel gas. The primary gas comprises the majority of the inflation fluid that inflates the air bag 12. The fuel gas, when ignited, heats the primary gas.

The combustible mixture of gases 18 may have any suitable composition known in the art, but preferably has a composition in accordance with the invention set forth in U.S. Pat. No. 5,348,344, to Blumenthal et al., entitled APPARATUS FOR INFLATING A VEHICLE OCCUPANT RESTRAINT USING A MIXTURE OF GASES, and assigned to TRW Vehicle Safety Systems Inc. The storage pressure in the chamber 20 may vary, but is preferably within the range of approximately 1,500 psig to approximately 5,000 psig., and is most preferably approximately 2,500 psig.

The apparatus 10 further includes a crash sensor 22 and an electrically actuatable igniter 24. As shown schematically in FIG. 1, the crash sensor 22 and the igniter 24 are included in an electrical circuit 26 with a power source 28. The power source 28 is preferably the vehicle battery and/or a capacitor. The crash sensor 22 includes a normally open switch 30. As known in the art, the crash sensor 22 monitors vehicle conditions to sense a vehicle condition indicating the occurrence of a crash. The crash-indicating condition may comprise, for example, sudden vehicle deceleration that is caused by a crash. If the crash-indicating condition is at or above a predetermined threshold level, it indicates the occurrence of a crash having at least a predetermined threshold level of severity. The threshold level of crash severity is a level at which inflation of the air bag 12 is desired to help protect an occupant of the vehicle. The switch 30 then closes and an actuating level of electric current is directed through the igniter 24 to actuate the igniter 24.

When the igniter 24 is actuated, it ignites the fuel gas in the mixture of gases 18. As the fuel gas burns, the pressure in the storage chamber 20 rises due to warming of the gases by the heat of combustion created by burning of the fuel gas. A rupturable closure wall 32 bursts open when the increasing pressure in the storage chamber 20 reaches a predetermined elevated level. The warm inflation gas then flows outward from the storage chamber 20 and into the air bag 12 to inflate the air bag 12.

Figure 2:
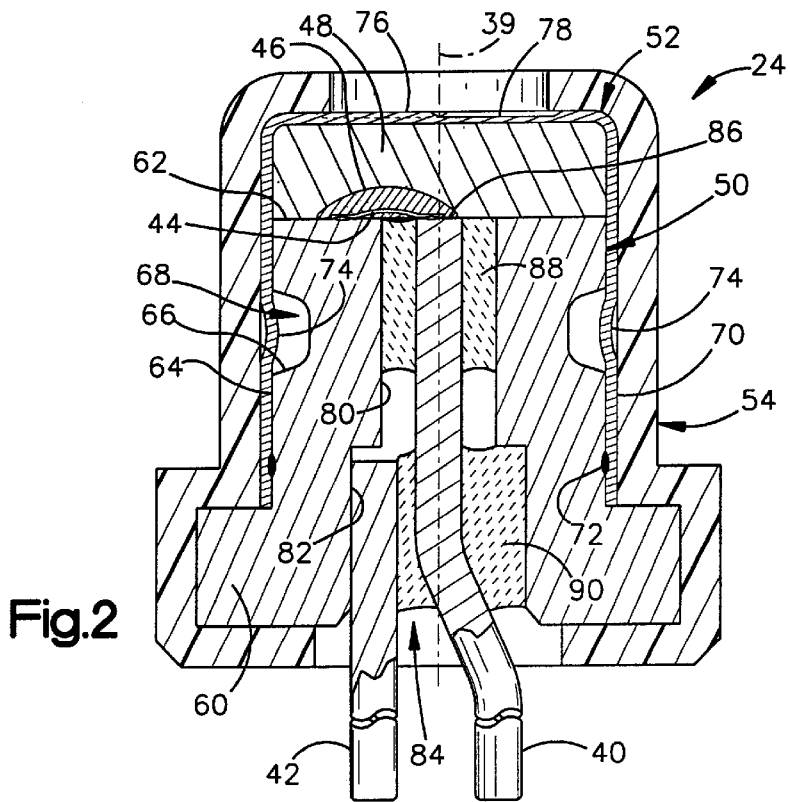
FIG. 2 is an enlarged sectional view of an igniter included in the apparatus of FIG. 1.

As shown in detail in FIG. 2, the igniter 24 is a generally cylindrical part with a central axis 39 and a pair of axially projecting electrode pins 40 and 42. An ohmic (resistive) heating element in the form of a bridgewire 44 is connected between the electrode pins 40 and 42 within the igniter 24. The bridgewire 44 may be formed of any suitable metal material known in the art. A small charge of pyrotechnic material in the form of an ignition droplet 46 adjoins the bridgewire 44. A main pyrotechnic charge 48 adjoins the ignition droplet 46. The pyrotechnic materials of which the ignition droplet 46 and the main pyrotechnic charge 48 are formed, including any non-pyrotechnic binders or other ingredients, may have any suitable compositions known in the art.

When the igniter 24 is actuated, as described above with reference to FIG. 1, the actuating level of electric current is directed through the igniter 24 between the electrode pins 40 and 42. As the actuating level of electric current is conducted through the bridgewire 44, the bridgewire 44 resistively generates heat which is transferred directly to the ignition droplet 46. The ignition droplet 46 is then ignited and produces combustion products including heat, hot gases and hot particles which ignite the main pyrotechnic charge 48. The main pyrotechnic charge 48 produces additional combustion products which are spewed outward from the igniter 24 and into the combustible mixture of gases 18 (FIG. 1) to ignite the fuel gas.

The parts of the igniter 24 shown in FIG. 2 further include a header 50, a charge cup 52 and a casing 54. The header 50 is a cylindrical metal part with a circular flange 60 projecting radially from one end. A planar surface 62 at the opposite end of the header 50 has an annular configuration centered on the axis 39. A cylindrical side surface 64 of the header 50 has a recessed portion 66 defining a circumferentially extending groove 68.

The charge cup 52 also is a metal part, and has a cylindrical side wall 70 received closely over the header 50. The side wall 70 of the charge cup 52 is fixed and sealed to the header 50 by a circumferentially extending weld 72. The charge cup 52 is further secured to the header 50 by a plurality of circumferentially spaced portions 74 of the side wall 70 which are crimped radially inward into the groove 68. In this arrangement, the side wall 70 and a circular end wall 76 of the charge cup 52 together contain and hold the main pyrotechnic charge 48 against the end surface 62 of the header 50.

A plurality of thinned portions 78 of the end wall 76, one of which is shown in FIG. 2, extend radially outward from the axis 39. The thinned portions 78 of the end wall 76 function as stress risers which rupture under the influence of the combustion products generated by the main pyrotechnic charge 48 when the igniter 24 is actuated. The casing 54 is a sleeve-shaped plastic part which is shrink fitted onto the header 50 and the ignition cup 52 so as to insulate and partially encapsulate those parts.

As further shown in FIG. 2, the header 50 has a pair of cylindrical inner surfaces 80 and 82 which together define a central passage 84 extending fully through the header 50. The first electrode pin 40 extends inward along the entire length of the central passage 84. A planar end surface 86 of the first electrode pin 40 is coplanar with the end surface 62 of the header 50. A pair of axially spaced apart glass seals 88 and 90 support the first electrode pin 40 in the central passage 84, and electrically insulate the first electrode pin 40 from the header 50. The second electrode pin 42 extends partly into the central passage 84 in contact with the second cylindrical inner surface 82 of the header 50. The second glass seal 90 insulates the electrode pins 42 and 40 from one another.

Figure 3:
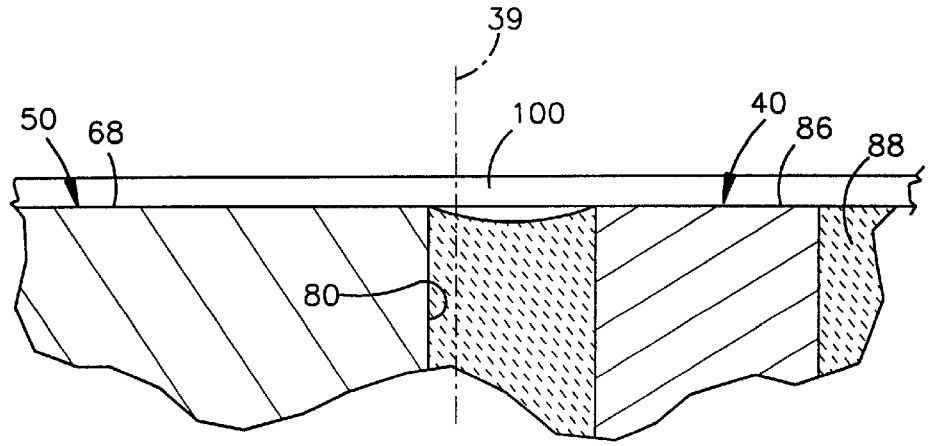
FIG. 3 is an enlarged partial view showing the igniter of FIG. 2 in a partially assembled condition.
Figure 4:
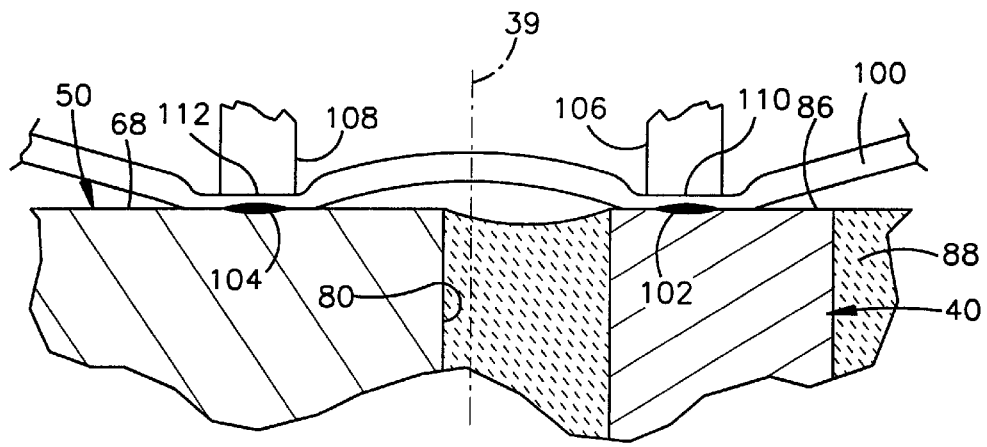
FIGS. 4 and 5 are views similar to FIG. 3 showing the igniter in more fully assembled conditions.
Figure 5:
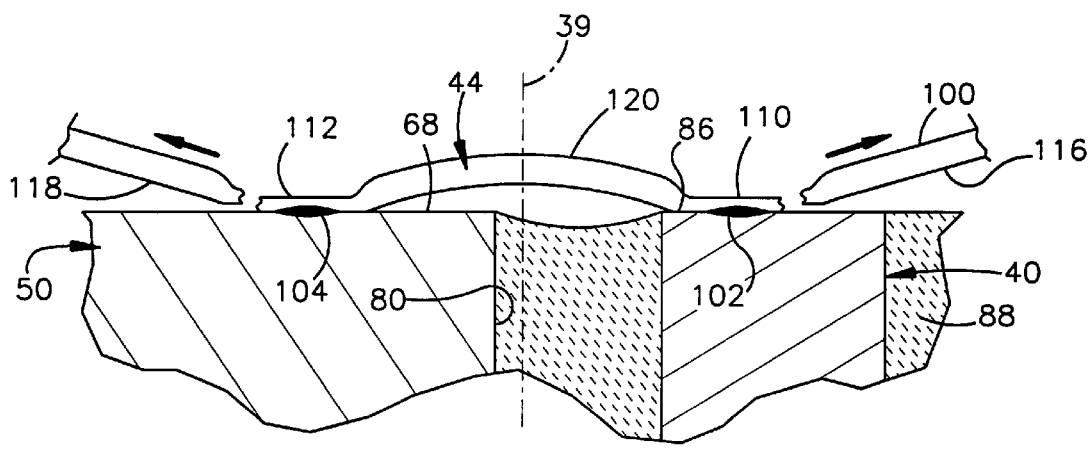

The bridgewire 44 is connected between the electrode pins 40 and 42 in the manner shown in FIGS. 3–5. Specifically, the bridgewire 44 is connected directly between the first electrode pin 40 and the header 50 which, as described above, contacts the second electrode pin 42.

A section of wire 100 is first placed across the first electrode pin 40 and the header 50, as shown in FIG. 3. A pair of electrical resistance spot welds 102 and 104 are then formed by a corresponding pair of welding electrodes 106 and 108, as shown in FIG. 4. The first weld 102 fixes the wire 100 to the first electrode pin 40 at the end surface 86 of the first electrode pin 40. The second weld 104 fixes the wire 100 to the header 50 at the end surface 62 of the header 50. When the wire 100 is heated resistively upon formation of the welds 102 and 104, the pressure applied by the welding electrodes 106 and 108 causes the wire 100 to become flattened between the welding electrodes 106 and 108 and the end surfaces 86 and 62. The first weld 102 is thus formed between a first flattened portion 110 of the wire 100 and the end surface 86 of the first electrode pin 40. The second weld 104 is likewise formed between a second flattened portion 112 of the wire 100 and the end surface 62 of the header 50. The heat and pressure of the welding process further cause the wire 100 to deform into a bowed configuration between the flattened portions 110 and 112.

As shown in FIG. 5, the sections 116 and 118 of the wire 100 that extend oppositely away from the flattened portions 110 and 112 are severed from the flattened portions 110 and 112. This is preferably accomplished merely by pulling those sections 116 and 118 of the wire 100 until they break away from the flattened portions 110 and 112. The bridgewire 44 is thus formed with an unflattened major portion 120 extending in an arc between a pair of flattened opposite end portions 110 and 112.

Figure 6:
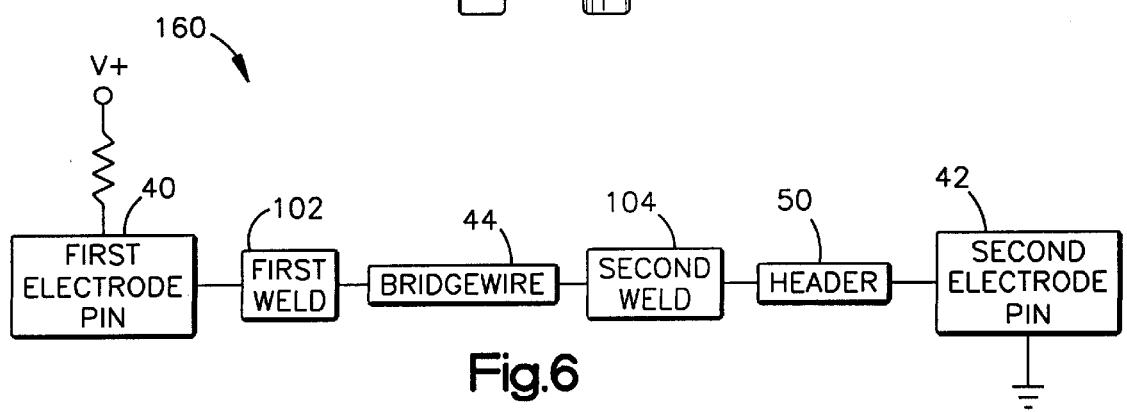
FIG. 6 is a schematic view of an electrical test circuit including parts of the igniter that are shown in FIG. 5.

If the welds 102 and 104 are strong enough to remain intact when the adjacent sections 116 and 118 of the wire 100 are broken away, they are strong enough to retain the bridgewire 44 in place within the fully assembled igniter 24 (FIG. 2) throughout the life of the igniter 24. However, this test of the weld strength does not indicate the locations, if any, where resistive heating of the bridgewire 44 or the welds 102 and 104 may vary from specified levels when the actuating level of electric current is directed through the igniter 24 in response to a vehicle crash. Therefore, the method of assembling the igniter 24 in accordance with the present invention includes additional steps in which the partially assembled structure of FIG. 5 is inspected with reference to resistive heating of the bridgewire 44 and the welds 102 and 104. These steps include connecting the partially assembled structure of FIG. 5 in an electrical test circuit 160, as shown schematically in FIG. 6.

The test circuit 160 is used to direct a test level of electric current through the bridgewire 44 and the welds 102 and 104. The test level of electric current is not great enough to cause the bridgewire 44 to fuse, but is great enough to cause the bridgewire 44 and the welds 102 and 104 resistively to generate heat which results in the emission of measurable amounts of infrared radiation.

Figure 7:
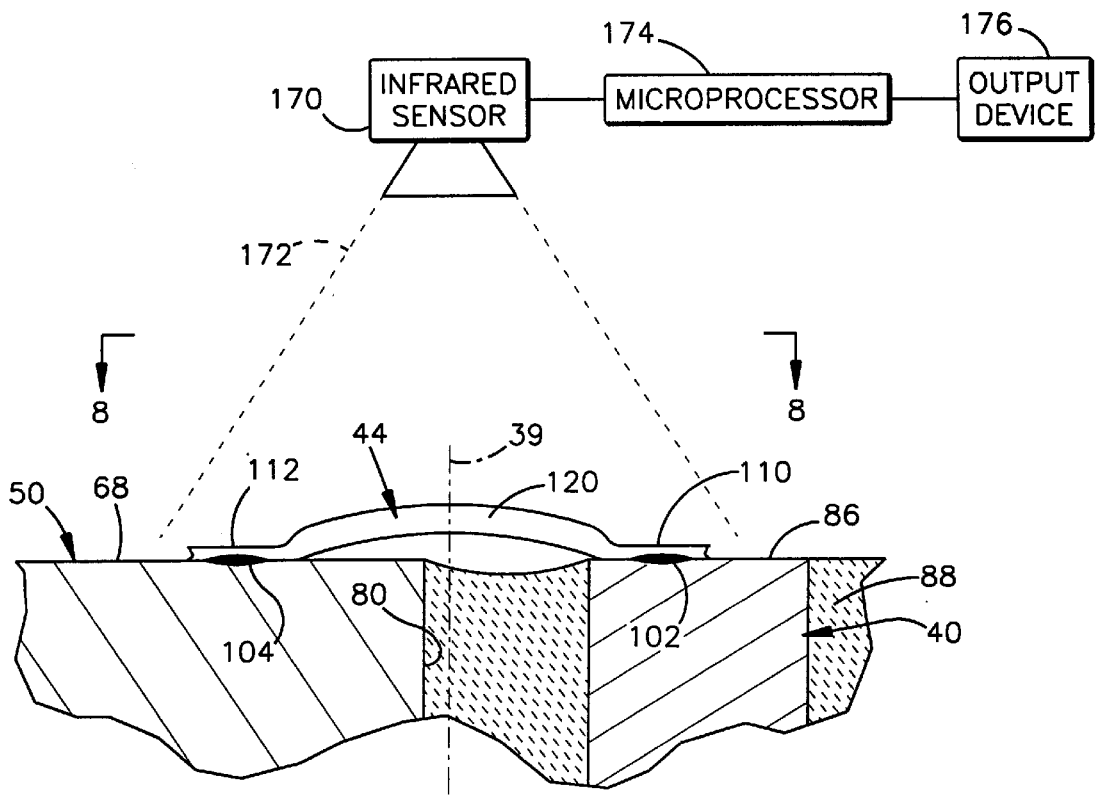
FIG. 7 is a view which is similar to FIG. 5, and which further shows an infrared sensing apparatus used in accordance with the present invention.
Figure 8:
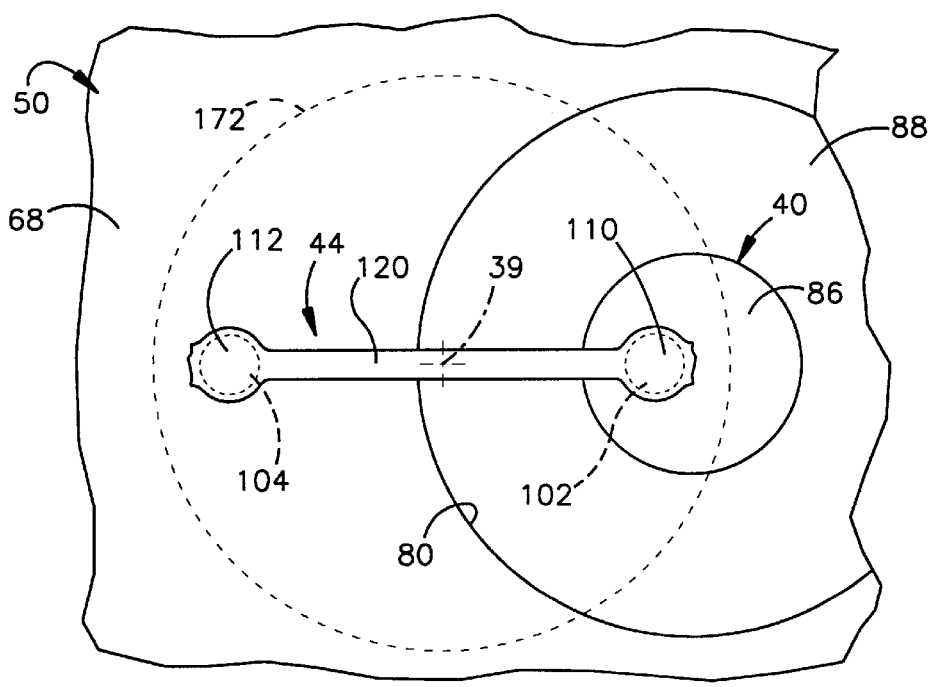
FIG. 8 is a view taken on line 8—8 of FIG. 7.

As shown in FIG. 7, an infrared sensor 170 is used to sense the infrared radiation emitted by the bridgewire 44 and the welds 102 and 104 under the influence of the test level of electric current. The sensor 170 in the preferred embodiment of the present invention is an infrared image scanning device. Such a device senses infrared radiation at selected points within a scanned field. The output of the sensor 170 is an electrical signal indicating the distribution and level of infrared radiation at selected points within the scanned field, and hence the distribution and level of surface temperatures at selected points within the scanned field. Further in accordance with the present invention, the sensor 170 scans a field 172 (FIG. 8) which is large enough to encompass fully the entire bridgewire 44, the underlying welds 102 and 104, and adjacent portions of the surfaces 86 and 62 upon which those parts are mounted.

A microprocessor 174 interprets and responds to the output of the sensor 170 by directing an output device 176 to produce one or more representations of the infrared radiation sensed by the sensor 170. Such representations may have any suitable format known in the art such as, for example, thermal images on the screen of a cathode ray tube. The output device 176, as well as the microprocessor 174, may thus comprise any suitable apparatus known in the art.

The representations of infrared radiation provided by the output device 176 indicate the sensed levels of infrared radiation emitted by the bridgewire 44 and the welds 102 and 104. The representations of the sensed levels of radiation emitted by the bridgewire 44 and the welds 102 and 104 are compared. The bridgewire 44 and welds 102 and 104 are accepted if the representations indicate that the sensed level of infrared radiation emitted by one or both of the welds 102 and 104 is not greater than the sensed level of infrared radiation emitted by the bridgewire 44. More specifically, the bridgewire 44 and welds 102 and 104 are accepted if the highest sensed level of infrared radiation (i.e hottest area) is centered approximately at the midpoint of the bridgewire 44. The ignition droplet 46 is then centered at the mid-point of the bridgewire, and the main pyrotechnic charge 48 and the other parts shown in FIG. 2 are installed to complete the assembly of the igniter 24.

A sensed level of infrared radiation emitted by one or both of the welds 102 and 104 greater than the sensed level of infrared radiation emitted by the bridgewire 44, is indicative of poor bonding of the bridgewire 44 to one or both of the welds 102 and 104 or thinning of the bridgewire 44 adjacent to the welds 102 and 104. An igniter 24 which has a greater sensed level of radiation at one or more of the weld 102 and 104 would then be rejected.

From the above description of the invention, those skilled in the art will perceive improvements, changes and modifications. For example, the microprocessor 174 could perform the comparison of the sensed levels of infrared radiation with the specified levels. The output device 176 could then provide a signal indicating the result. Such improvements, changes and modifications within the skill of the art are intended to be covered by the appended claims.

Having described the invention, the following is claimed:

1. A method of assembling an igniter for a gas generating composition for vehicle occupant restraint comprising the steps of:

providing a pair of spaced apart electrodes;

providing a heat ignitable material;

spot electrical resistance welding a heating element to said electrodes, said heating element having flattened portions at said spot welds and a central portion between said spot welds adapted for contact with said heat ignitable material;

directing a test level of electric current between said electrodes and through said heating element and said spot welds at a level effective to heat said heating element and said spot welds;

sensing the level of infrared radiation emitted by said heating element and said spot welds, throughout a scanned field which fully encompasses said heating element and said welds, under the influence of said test level of electric current;

comparing the sensed levels of infrared radiation emitted by said spot welds and emitted by said heating element;

installing said heat ignitable material approximately at the mid-point of the heating element in heat transferring relationship with the heating element if the sensed level of radiation emitted by one or both of the said welds is not significantly greater than the sensed level of infrared radiation emitted by said heating element.

2. The method of claim 1 wherein the infrared radiation is sensed by an infrared image scanning device.

3. The method of claim 2, further comprising the step of producing one or more representations of the sensed levels of infrared radiation, wherein the one or more representation is a thermal image of said spot welds and said heating element.

4. A method of assembling an igniter for a gas generating composition for vehicle occupant restraint comprising the steps of:

providing a pair of spaced apart electrodes;

providing a heat ignitable material;

spot electrical resistance welding a heating element to said electrodes, said heating element having flattened portions at said spot welds and a central portion between said spot welds adapted for contact with said heat ignitable material;

directing a test level of electric current between said electrodes and through said heating element and said spot welds at a level effective to heat said heating element and said spot welds;

sensing the level of infrared radiation emitted by said heating element and said spot welds, throughout a scanned field which fully encompasses said heating element and said welds, under the influence of said test level of electric current;

comparing the sensed levels of infrared radiation at selected points within the scanned field;

installing said heat ignitable material approximately at the mid-point of heating element in heat transferring relationship with the heating element if the highest sensed level of infrared radiation is centered approximately at the mid-point of the heating element.

5. The method of claim 4 wherein the selected points within the scanned field are said spot welds and said heating element.

* * * * *